United States Patent
Zhang et al.

(10) Patent No.: US 11,278,557 B2
(45) Date of Patent: Mar. 22, 2022

(54) GLUCOSE PELLETS, PREPARATION METHOD AND USE THEREOF

(71) Applicant: COSCI MED-TECH CO. LTD., Beijing (CN)

(72) Inventors: Changqing Zhang, Beijing (CN); Dezhi Zhu, Beijing (CN); Shenghai Zhang, Beijing (CN); Jie Ning, Beijing (CN); Xiaoyan Xian, Beijing (CN)

(73) Assignee: COSCI MED-TECH CO. LTD., Beijing (CN)

( * ) Notice: Subject to any disclaimer, the term of this patent is extended or adjusted under 35 U.S.C. 154(b) by 141 days.

(21) Appl. No.: 16/494,013

(22) PCT Filed: Mar. 16, 2017

(86) PCT No.: PCT/CN2017/076869
§ 371 (c)(1),
(2) Date: Sep. 13, 2019

(87) PCT Pub. No.: WO2018/165930
PCT Pub. Date: Sep. 20, 2018

(65) Prior Publication Data
US 2021/0121487 A1     Apr. 29, 2021

(51) Int. Cl.
*A61K 31/7004* (2006.01)
*A61K 9/16* (2006.01)

(52) U.S. Cl.
CPC ........ *A61K 31/7004* (2013.01); *A61K 9/1635* (2013.01); *A61K 9/1652* (2013.01); *A61K 9/1682* (2013.01)

(58) Field of Classification Search
CPC .............. A61K 31/7004; A61K 9/1682; A61K 9/1652; A61K 9/1635
USPC ......................................................... 514/23
See application file for complete search history.

(56) References Cited

U.S. PATENT DOCUMENTS 5,360,614 A * 11/1994 Fox et al.
2016/0081941 A1    3/2016 Neumann et al.

FOREIGN PATENT DOCUMENTS

| CN | 103432082 A | 12/2013 |
| JP | 01-230513 A | 9/1989 |
| JP | H-823922 A | 1/1996 |
| JP | 2000-516613 A | 12/2000 |
| JP | 2006-001941 A | 1/2006 |
| WO | WO 2014/180453 | * 11/2014 |

OTHER PUBLICATIONS

Hu, Guihua, et al., 1 Case Analysis of Hepatic Glycogen Accumulation Complicated with Diabetes, Chinese Journal of Misdiagnostics, Feb. 28, 2009, 6(9), pp. 1500-1501.
International Search Report and Written Opinion for International Appl. No. PCT/CN2017/076869, dated Dec. 22, 2017.
Franc, Ales, et al.: "Preparation of pellets with controlled release of glucose as prevention of hypoglycaemia in paedriatic patients", European Journal of Pharmaceutical Sciences, Mar. 21, 2015, 9 Pages, Elsevier B.V., Czech Republic, www.elsevier.com/locate/ejps.
Nozomi Casket: "Gluco Pellets, their production methods and their use" 2019-572268; Aug. 12, 830.

* cited by examiner

*Primary Examiner* — Yih-Horng Shiao
(74) *Attorney, Agent, or Firm* — Foley & Lardner LLP (57) ABSTRACT

The invention belongs to the field of biomedicine, and particularly relates to a glucose core, comprising a glucose and/or a glucose hydrate, a diluent and a binder, wherein, the glucose and/or the glucose hydrate is present in the glucose core in an amount of ≤85% by weight percentage; and relates to a glucose pellet comprising the glucose core and a laminated layer coating the glucose core; and further relates to a pharmaceutical composition comprising the glucose pellet. The glucose pellet or the pharmaceutical composition of the invention are useful in treatment and/or assistant treatment of a glycogen storage disease and/or a diabetes.

18 Claims, 1 Drawing Sheet

GLUCOSE PELLETS, PREPARATION METHOD AND USE THEREOF

CROSS-REFERENCE TO RELATED APPLICATIONS

This application is a 35 U.S.C. 371 National Stage Application of International Application No. PCT/CN2017/076869, filed on Mar. 16, 2017, the contents of which are hereby incorporated by reference in their entirety.

TECHNICAL FIELD

The invention belongs to the field of biomedicine, and relates to glucose pellets, a preparation method thereof and use thereof. In particular, the present invention relates to glucose sustained-release pellets, a preparation method thereof and use thereof.

BACKGROUND ART

Glycogen storage disease (GSD) is a disorder of glycogen metabolism which is caused by a congenital enzyme deficiency, but the differences in types of such enzyme deficiency result in complex types of the disease. Glycogen storage disease is a rare disease, and the incidence of the disease in Europe is about 1/20000 to 1/25000.

Glycogen is a macromolecular polysaccharide composed of glucose units, and mainly stored in liver and muscle as spare energy, and normal liver and muscle store about 4% and 2% glycogen, respectively. The process of glycogen synthesis comprises: glucose ingested in body forms uridine diphosphate glucose (UDPG) under the catalysis of glucokinase, glucose phosphate mutase and uridine diphosphate glucose pyrophosphorylase; then glucose molecules provided by UDPG are linked into a long chain by glycogen synthetase using α-1,4-glycosidic bonds; the 1,4-bond is transferred to 1,6-bond by branching enzyme every 3 to 5 glucose residues in order to form branches, and such expansion eventually results in the formation of a macromolecule with dendritic structure. The molecular weight of glycogen is up to several millions, and the glucose linear chains in its outermost layer are relatively long, usually having 10 to 15 glucose units. The decomposition of glycogen is mainly catalyzed by phosphorylase, releasing glucose 1-phosphate from the glycogen molecule; however, the role of phosphorylase is limited to 1,4-glycosidic bonds, and when there are only 4 glucose residues before the branching point, the three residues among them must be transferred to other linear chains by debranching enzyme (starch 1,6-glucosidase) to ensure the role of the phosphorylase continues; at the same time, the debranching enzyme can release the last glucose molecule linked by α-1,6-glycosidic bond; and this is repeated to ensure the body's demand for glucose. The α-1,4-glucosidase (acid maltase) present in lysosomes can also hydrolyze glucose linear chains of different lengths into oligosaccharide molecules such as maltose. During the above synthesis and decomposition processes of glycogen, the deficiency of any enzyme may result in various types of glycogen storage diseases with different clinical manifestations.

Patients with GSD cannot synthesize or metabolize glycogen normally due to the lack of relevant enzymes in the body, which impedes glycogen synthesis or decomposition and leads to the deposition of glycogen in tissues. There are at least 8 types of enzymes necessary for glycogen synthesis and catabolism. Glycogen metabolism diseases can be classified into at least 13 clinical types due to different types of enzyme deficiency, among which types I, III, IV, VI and IX predominantly manifest liver lesions; and types II, III, V and VII predominantly manifest muscle tissue involvements. Among them, type II of early-type glycogen storage disease usually develops within 1 year old, involving multiple organs, especially heart, which can be fatal. The main clinical manifestations of glycogen storage disease are hepatomegaly and hypoglycemia, including type Ia (glucose-6-phosphatase deficiency) and more rare type Ib (G-6-P microsomal transferase deficiency), type III, type VI, and phosphatase β-kinase deficiency with X-chromosomal and autosomal recessive inheritance. The glycogen storage disease of muscular energy disorder is mainly characterized by muscle atrophy, muscular hypotonia, and dyskinesia, including type III, type V, type VII, otherwise glycerol phosphate mutase deficiency and LDHM subunit deficiency have type II and type IV, etc.

Glycogen storage disease is a hereditary disease, and occurs when a child is born. With the increase of age, obvious hypoglycemia symptoms, such as weakness, sweating, vomiting, convulsions, coma, and even ketoacidosis, may appear, and hepatosplenomegaly may appear due to the gradual accumulation of glycogen. The child has growth retardation, intellectual barrier-free, short stature, obesity, pale yellow skin, abdominal bulging, markedly enlarged and hard texture liver, poor muscle development, weakness, especially at lower limbs. Most patients of such disease can't survive to adulthood, and often die from acidosis and coma, and mild cases may get better in adulthood.

Clinical treatment of the disease is mainly based on diet guidance and raw corn starch treatment. The basic principle is to maintain blood sugar at a relatively stable normal level, avoiding as much as possible the increase of glycogen accumulation caused by excessive hyperglycemia after eating, avoiding symptoms of limosis hypoglycemia caused by the patient's inability in glycogen metabolism, and avoiding a series of complications caused by fluctuations in blood glucose (serious complications may be life-threatening). In general, the diet guidance comprises: frequently eating high-protein, low-fat, low-sugar foods in small amounts to maintain normal blood sugar level; particularly, one additional meal at midnight is necessary to avoid hypoglycemia in the next morning. Other treatments include preventing infection, correcting acidosis, and the like. Raw corn starch treatment is currently the most common method for the treatment of glycogen storage disease, especially for infants and children, and the number of patients receiving this treatment is estimated to be 20,000 to 50,000 in Asia, and about 10,000 to 30,000 in China. The principle of the raw corn starch treatment is to release glucose slowly and continuously through the digestion thereof in human body, thereby maintaining the blood sugar level of the patient.

Although the cost of the raw corn starch treatment is low, the administration method thereof has many drawbacks:

1) Too many times of taking: no less than 4 times per day, usually taking between two meals, especially at about 3 am at night;

2) Harsh conditions for taking: be sure to take "raw" corn starch instead of cooked corn starch or cornmeal porridge, and further be sure to take it with cold water, so that its acceptance level in patients is low;

3) Large dosage: due to the volume expansion of raw corn starch after being taken with cold water, it is very difficult for children to take a therapeutic amount of raw corn starch at one time;

4) Poor tolerance: diarrhea is easily caused by the digestive system intolerance in infants;

5) Poor compliance: the administration method is complicated, and the long-term administration brings inconvenience to daily life;

6) The quality of commercially available raw corn starch is uneven, resulting in unstable treatment effect;

7) The ingredients for maintaining sustained release in raw corn starch are less, and thus the dosage is increased.

In summary, although raw corn starch therapy has the advantage of low cost, its inherent drawbacks limit its application.

There is a need for a new drug that can be used in treatment and/or adjuvant treatment of glycogen storage disease.

CONTENTS OF THE INVENTION

The inventors have prepared a glucose core with suitable particle size and smooth surface, and further prepared a glucose pellet with suitable particle size distribution, high roundness and smooth surface. On this basis, the inventors have also developed a glucose sustained-release pellet, which can release glucose continuously and slowly, maintain blood sugar of patients at a normal level, and achieve treatment and/or adjuvant treatment of glycogen storage disease. The glucose sustained-release pellet of the invention also has the effect of treatment or adjuvant treatment on diabetes, which is convenient to take, and has good mouthfeel, good tolerance and good compliance.

A first aspect of the invention relates to a glucose core comprising the following components:

a glucose (preferably anhydrous glucose) and/or a glucose hydrate, a diluent and a binder;

wherein, as calculated by weight percentage, the glucose and/or the glucose hydrate is present in the glucose core in an amount of ≤85%, preferably 30% to 80%, more preferably 30%, 36%, 49%, 50%, 60%, 61%, 65%, 67%, 70%, 74%, 78%, 80%, 81% or 85%.

In certain embodiments of the present invention, the glucose and/or the glucose hydrate has a particle size of ≤110 mesh, preferably ≤120 mesh, more preferably ≤130 mesh, ≤140 mesh or ≤150 mesh.

In certain embodiments of the present invention, the glucose hydrate is glucose monohydrate.

In certain embodiments of the present invention, the diluent comprises a microcrystalline cellulose; optionally, it further comprises a starch.

In certain embodiments of the present invention, the microcrystalline cellulose has a particle diameter of 20 to 100 μm.

In certain embodiments of the present invention, the microcrystalline cellulose has a water content of 1.5% to 6.0% (W/W), preferably 1.5% to 4% (W/W).

In certain embodiments of the present invention, the microcrystalline cellulose is MCC101 produced by JRS, Germany.

In certain embodiments of the present invention, the microcrystalline cellulose is present in the glucose core in an amount of 10% to 60%, preferably 15% to 50%, more preferably 10%, 11.4%, 12%, 16%, 18.7%, 19%, 22%, 24%, 27%, 29.7%, 30%, 33%, 37%, 40%, 42%, 46%, 47%, 50%, as calculated by weight percentage.

In certain embodiments of the present invention, the starch is present in the glucose core in an amount of 0% to 13%, preferably 0% to 10%, more preferably 0%, 1.5%, 2%, 6%, 8%, 10%, as calculated by weight percentage.

In certain embodiments of the present invention, the binder is one or more selected from the group consisting of polyvinylpyrrolidone, hydroxypropylmethylcellulose, hydroxypropylcellulose, sodium carboxymethylcellulose, starch slurry, dextrin, gum arabic, ethylcellulose and konjac flour, and preferably is polyvinylpyrrolidone.

In certain embodiments of the present invention, the polyvinylpyrrolidone has a number average molecular weight of 30,000 to 70,000, preferably 40,000 to 60,000, more preferably 50,000.

In certain embodiments of the present invention, the polyvinylpyrrolidone is PVPK29/32 manufactured by Ashalnd.

In certain embodiments of the present invention, the binder is present in the glucose core in an amount of 1.0% to 5.0%, preferably 1%, 1.2%, 1.3%, 1.5%, 1.6%, 1.7, 2%, 2.1%, 2.3%, 2.6%, 2.8%, 3%, 3.4%, 4%, 4.7%, 5%, as calculated by weight percentage.

In certain embodiments of the present invention, the glucose core further comprises a solvent.

In certain embodiments of the present invention, the solvent is selected from the group consisting of water and/or alcohol.

In certain embodiments of the present invention, the solvent is present in the glucose core in an amount of 15.0% to 25.0%, preferably 15%, 17%, 19%, 20%, 21%, 23% or 24%, by weight percentage.

In certain embodiments of the present invention, the glucose core has a particle diameter of 100 to 300 μm, preferably 150 to 250 μm, more preferably 152 to 250 μm, 156 μm, 158 μm, 160 μm, 170 μm, 180 μm, 200 μm, 220 μm, 230 μm or 240 μm.

A second aspect of the present invention relates to a glucose pellet comprising any one of the glucose cores according to the first aspect of the invention and a laminated layer coating the glucose core.

In certain embodiments of the second aspect of the present invention, the laminated layer comprises the following components: a glucose (preferably anhydrous glucose) and/or a glucose hydrate, a diluent, and a binder.

In certain embodiments of the second aspect of the present invention, the glucose and/or the glucose hydrate is present in the laminated layer in an amount greater than the amount of the glucose and/or the glucose hydrate in the glucose core.

In certain embodiments of the second aspect of the present invention, the glucose and/or the glucose hydrate is present in the laminated layer in an amount of ≥70%, preferably 75% to 90%, more preferably 75%, 77%, 79%, 80%, 81%, 82%, 85%, 86%, 88% or 90%, as calculated by weight percentage.

In certain embodiments of the second aspect of the present invention, the glucose and/or the glucose hydrate in the laminated layer has a particle size of ≤110 mesh, preferably ≤120 mesh, more preferably ≤130 mesh, ≤140 mesh or ≤150 mesh.

In certain embodiments of the second aspect of the present invention, the glucose hydrate in the laminated layer is glucose monohydrate.

In certain embodiments of the second aspect of the present invention, the diluent in the laminated layer is a microcrystalline cellulose and a starch.

In certain embodiments of the second aspect of the present invention, the microcrystalline cellulose in the laminated layer has a particle diameter of 20 to 100 μm.

In certain embodiments of the second aspect of the present invention, the microcrystalline cellulose in the laminated layer has a water content of 1.5% to 6.0% (W/W), preferably 1.5% to 4% (W/W).

In certain embodiments of the second aspect of the present invention, the microcrystalline cellulose in the laminated layer is MCC101 produced by JRS, Germany.

In certain embodiments of the second aspect of the present invention, the microcrystalline cellulose is present in the laminated layer in an amount of 1% to 15%, preferably 2% to 11%, more preferably 2%, 2.4%, 2.7%, 3%, 3.6%, 4%, 4.2%, 4.8%, 5%, 5.1%, 5.6%, 6%, 6.6%, 7%, 7.3%, 8%, 8.5%, 9%, 9.6%, 10%, 11%, 14%, as calculated by weight percentage.

In certain embodiments of the second aspect of the present invention, the starch is present in the laminated layer in an amount of 1% to 10%, preferably 2% to 8%, more preferably 2%, 2.3%, 2.7%, 3%, 3.2%, 4%, 4.5%, 4.9%, 5%, 5.7%, 6%, 6.4%, 7%, 7.3% or 8%, as calculated by weight percentage.

In certain embodiments of the second aspect of the present invention, the binder in the laminated layer is one or more selected from the group consisting of polyvinylpyrrolidone, hydroxypropylmethylcellulose, hydroxypropylcellulose, sodium carboxymethylcellulose, starch slurry, dextrin, gum arabic, ethylcellulose and konjac flour, preferably is polyvinylpyrrolidone.

In certain embodiments of the second aspect of the present invention, the polyvinylpyrrolidone has a number average molecular weight of 30,000 to 70,000, preferably 40,000 to 60,000, more preferably 50,000.

In certain embodiments of the second aspect of the present invention, the polyvinylpyrrolidone is PVPK29/32 manufactured by Ashland.

In certain embodiments of the second aspect of the present invention, the binder is present in the laminated layer in an amount of 1.0% to 3.0%, preferably 0.4%, 1%, 1.2%, 1.4%, 1.6%, 2%, 2.2%, 2.8%, 3%, as calculated by weight percentage.

In certain embodiments of the second aspect of the present invention, the glucose pellet has a particle size of 15 to 50 mesh, preferably 18 to 40 mesh, more preferably 20 to 30 mesh, 30 to 40 mesh, 20 to 40 mesh, 20 mesh, 24 mesh, 27 mesh, 32 mesh, 36 mesh, 38 mesh, 40 mesh or 50 mesh.

In certain embodiments of the second aspect of the present invention, the glucose pellet is a glucose sustained-release pellet.

In certain embodiments of the second aspect of the present invention, the glucose sustained-release pellet comprises any one of the glucose pellets according to the second aspect of the invention, and a sustained-release coating which is coated on the glucose pellet.

In certain embodiments of the second aspect of the present invention, the sustained-release coating comprises a film-forming agent, a porogen and a plasticizer.

In certain embodiments of the second aspect of the present invention, the sustained-release coating further comprises an additional excipient.

In certain embodiments of the second aspect of the present invention, the film-forming agent is one or more selected from the group consisting of ethylcellulose, cellulose acetate, and acrylic resin, preferably is ethylcellulose.

In certain embodiments of the second aspect of the present invention, the film-forming agent is present in the sustained-release coating in an amount of 60% to 80%, preferably 60%, 63%, 68%, 70%, 72%, 76% or 80%, as calculated by weight percentage.

In certain embodiments of the second aspect of the present invention, the porogen is present in the sustained-release coating in an amount of 8% to 20%, preferably 8%, 10%, 12%, 14%, 15%, 16%, 18% or 20%, as calculated by weight percentage.

In certain embodiments of the second aspect of the present invention, the plasticizer is present in the sustained-release coating in an amount of 10% to 23%, preferably 14%, 15%, 16%, 17%, 20%, 21% or 22%, as calculated by weight percentage.

In certain embodiments of the second aspect of the present invention, the porogen is one or more selected from the group consisting of hydroxypropylcellulose, polyvinylpyrrolidone, hydroxypropylmethylcellulose, talc, and polyethylene glycol.

In certain embodiments of the second aspect of the present invention, the plasticizer is one or more selected from the group consisting of triethyl citrate, tributyl citrate, dibutyl sebacate, polyethylene glycol, dimethyl phthalate and diethyl phthalate.

A third aspect of the present invention relates to a method for preparing any one of the glucose cores according to the first aspect of the invention, comprising the following steps:

(1-1) mixing a glucose (preferably anhydrous glucose) and/or a glucose hydrate with a diluent to obtain a mixture 1;

(1-2) dissolving a binder in a solvent to form a binder solution;

(1-3) mixing the binder solution with the mixture 1 to obtain a mixture 2;

(1-4) granulating the mixture 2 to obtain a glucose core; optionally, the method further comprises step (1-5): sieving the glucose core obtained in the step (1-4).

In certain embodiments of the present invention, in the step (1-2), the binder solution has a concentration of 1% to 60%, preferably 1% to 20%, more preferably 4%, 8%, 10%, 12% or 15%, as calculated by weight percentage.

In certain embodiments of the present invention, in the step (1-3), the binder solution is added to the mixture 1 in an atomizing manner and mixed.

A fourth aspect of the present invention relates to a method for preparing any one of the glucose pellets according to the second aspect of the invention, comprising the following steps for preparing a laminated layer:

(2-1) mixing a glucose (preferably anhydrous glucose) and/or a glucose hydrate with a diluent to obtain a mixture;

(2-2) dissolving a binder in a solvent to form a binder solution;

(2-3) performing lamination treatment of the glucose core with the mixture and the binder solution, and drying to obtain a glucose pellet;

optionally, the method further comprises step (2-4): sieving the glucose pellet obtained in the step (2-3).

In certain embodiments of the present invention, in the step (2-2), the binder solution has a concentration of 1% to 60%, preferably 1% to 20%, more preferably 2.5%, 3%, 5%, 7%, 8%, 9% or 10%, as calculated by weight percent.

In certain embodiments of the present invention, in the step (2-3), the weight ratio of the mixture to the glucose core is (1.5-6):1, preferably 1.5:1, 2.5:1, 3.5:1, or 5.0:1.

In certain embodiments of the present invention, in the step (2-3), the glucose core is added to a coating granulator at one time, and the mixture and the binder solution are continuously added to the coating granulator.

In certain embodiments of the present invention, in the step (2-3), the addition rate ratio of the mixture to the binder solution is $(1.36\text{-}2.25):1$ $(g\cdot min^{-1}/g\cdot min^{-1})$, preferably 1.4:1 $(g\cdot min^{-1}/g\cdot min^{-1})$, 1.64:1 $(g\cdot min^{-1}/g\cdot min^{-1})$, 1.7:1 $(g\cdot min^{-1}/g\cdot min^{-1})$ or 1.78:1 $(g\cdot min^{-1}/g\cdot min^{-1})$.

In certain embodiments of the present invention, the method further comprises a step of coating the glucose pellet.

In certain embodiments of the present invention, the method further comprises the following steps:

(3-1) formulating ethanol and water into an ethanol-water solution, dissolving a porogen in the ethanol-water solution, and adding a film-forming agent to obtain a solution;

(3-2) dissolving a plasticizer in the solution obtained in the step (3-1) to obtain a coating solution;

(3-3) coating the glucose pellet with the coating solution obtained in the step (3-2), and drying to obtain a glucose sustained-release pellet.

In certain embodiments of the present invention, in the step (3-1), the weight percentage of ethanol in the ethanol-water solution is 60% to 90%, preferably 80%.

In certain embodiments of the present invention, in the step (3-1), the weight of the ethanol-water solution is 50 to 250 times, preferably 60 times, 74 times, 118 times, 189 times or 200 times the weight of the porogen.

In certain embodiments of the present invention, in the step (3-1), the dissolution of the porogen and the film-forming agent is carried out under stirring.

In certain embodiments of the present invention, in the step (3-1), the dissolution time of the film-forming agent is 60 minutes or longer.

In certain embodiments of the present invention, in the step (3-2), the dissolution of the plasticizer is carried out under stirring.

In certain embodiments of the present invention, in the step (3-2), the dissolution time of the plasticizer is 40 to 60 minutes, preferably 40 minutes, 50 minutes or 60 minutes.

In certain embodiments of the present invention, in the step (3-3), the temperature of the glucose pellet during the coating process is 30 to 46° C., preferably 30° C., 36° C., 40° C., 42° C., 44° C. or 46° C.

In certain embodiments of the present invention, in the step (3-3), the drying temperature is 20 to 50° C., the drying time is 20 to 60 minutes; preferably, the drying temperature is 35° C., 40° C., 45° C. or 50° C.; preferably, the drying time is 30 minutes, 40 minutes or 50 minutes.

A fifth aspect of the present invention relates to a pharmaceutical composition comprising any one of the glucose pellets according to the second aspect of the invention; preferably, the pharmaceutical composition is a capsule or a tablet, more preferably a sustained-release pellet capsule or a tablet made of a sustained release pellet.

A sixth aspect of the present invention relates to a use of the glucose core according to any item of the first aspect of the invention, the glucose pellet of any item of the second aspect of the invention, or the pharmaceutical composition according to any item of the fifth aspect of the invention in manufacture of a medicament for treatment and/or adjuvant treatment of a glycogen storage disease or diabetes.

In certain embodiments of the present invention, the glycogen storage disease is one or more selected from the group consisting of glycogen storage disease type I, glycogen storage disease type II, glycogen storage disease type III, glycogen storage disease type IV, glycogen storage disease type V, glycogen storage disease type VI, glycogen storage disease type VII, disease of phosphatase b kinase deficiency (type VIII or IX), glycogen storage disease type X, and glycogen storage disease type O.

In certain embodiments of the present invention, the diabetes is type II diabetes.

A seventh aspect of the present invention relates to a method for treating a glycogen storage disease or a diabetes, comprising a step of administering to a subject in need thereof an effective amount of the glucose pellet according to any item of the second aspect of the invention or the pharmaceutical composition according to any item of the fifth aspect of the invention.

In certain embodiments of the present invention, the glycogen storage disease is one or more selected from the group consisting of glycogen storage disease type I, glycogen storage disease type II, glycogen storage disease type III, glycogen storage disease type IV, glycogen storage disease type V, glycogen storage disease type VI, glycogen storage disease type VII, disease of phosphatase b kinase deficiency (type VIII or IX), glycogen storage disease type X, and glycogen storage disease type O.

In certain embodiments of the invention, the diabetes is type II diabetes.

An eighth aspect of the present invention relates to a method for inhibiting glycogen accumulation or maintaining blood glucose stability, comprising a step of administering to a subject in need thereof an effective amount of the glucose pellet of any item of the second aspect of the invention or the pharmaceutical composition of any item of the fifth aspect of the invention.

In the present invention, unless otherwise specified:

The term "glucose hydrate" refers to glucose containing water of crystallization, which typically is glucose monohydrate ($C_6H_{12}O_6 \cdot H_2O$).

The term "core" refers to a material that is initially used to carry a laminated layer in a conventional "centrifugation-granulation process".

The term "diluent" is also called "filler"; it refers to an excipient that is used in conjunction with a main drug to facilitate the shaping of an intermediate or a formulation.

The term "binder" refers to an excipient that imparts tackness to a material with no or insufficient viscosity so as to coalesce the material.

The term "microcrystalline cellulose" is a commonly used diluent obtained by partial hydrolysis of plant cellulose. The microcrystalline cellulose of the present invention has a particle diameter of 20 to 100 μm, a water content of 1.5% to 6.0% (W/W), and a number average molecular weight of 26,000 to 43,000, preferably 30,000 to 40,000, more preferably 36,000.

The term "laminated layer" refers to a binder and a powder that gradually adhere to the surface of core during a pelletizing step of "centrifugation-granulation" process.

The term "pellet" refers to a spherical solid body composed of a drug powder and an excipient with an average particle diameter of less than 2.5 mm. Pellet is a dose-dispersible formulation, one dose often consists of a plurality of discrete units, usually tens or even more than one hundred pellets.

The term "sustained-release pellet" refers to a small pellet with sustained-release effect prepared by covering a pellet with a sustained-release film. The sustained-release pellet usually has an average particle diameter of less than 2.5 mm.

The term "film-forming agent" refers to a polymer capable of forming a continuous film.

The term "porogen" refers to an excipient that dissolves or drops off when it contacts with a dissolution medium or gastrointestinal fluid resulting in producing reticulate porous structures in a coating material.

The term "plasticizer" refers to a synthetic polymeric excipient that is widely used in the coating process and has the effect of lowering the film-forming temperature of a polymer and enhancing the flexibility of a film.

The term "lamination" refers to an operation of laminating a binder and a powder onto a core using a centrifugation-coating granulator.

The term "granulation" refers to an operation of processing a material into pellets with a certain shape and size.

The term "coating treatment" refers to an operation in which a coating solution is uniformly sprayed onto the surface of a pellet in spraying drops by a coating device, so as to achieve a desired weight gain and then form a plastic film layer with a thickness of several micrometers. After drying a film coating preparation is prepared.

Beneficial Effects

The present invention achieves at least one of the effects described below:

1. The glucose core prepared by the present invention has a suitable particle size and a smooth surface.

2. The glucose pellets prepared by the present invention have a suitable particle size distribution, a good roundness and a smooth surface.

3. The glucose sustained-release pellets prepared by the present invention are useful in treatment and/or assistant treatment of a glycogen storage disease, and have therapeutic effects on other diseases associated with blood glucose regulation, such as diabetes.

BRIEF DESCRIPTION OF THE DRAWINGS

In order to make the content of the present invention easier to understand, the present invention will be further described in the following examples with reference to the accompanying drawings, in which.

SPECIFIC MODELS FOR CARRYING OUT THE INVENTION

Example 1: Glucose Core A, Glucose Pellet A and Glucose Sustained-Release Pellet A 1. Preparation of Glucose Core A (1-1) Glucose monohydrate was pulverized, passed through a 120 mesh sieve, and the sieved portion was taken for subsequent steps. According to the formulation of Table 1, 614.0 g of glucose monohydrate and 371.0 g of MCC101 were added to a wet-mixing granulator and mixed uniformly;

(1-2) According to the formulation of Table 1, 15.0 g of PVPK29/32 was dissolved in 300.0 g of water to prepare a binder solution; the binder solution was sprayed into the wet-mixing granulator in atomization manner, and the glucose core A was obtained via granule preparation and granulation, and the content of the glucose monohydrate in the glucose core A was 49.1% (W/W).

TABLE 1

| Raw material | Weight (g) | Manufacturer |
|---|---|---|
| Glucose monohydrate | 614 | Xiwang Group Co., Ltd |
| MCC101 (microcrystalline cellulose) | 371 | JRS, Germany |
| PVPK29/32 (polyvinylpyrrolidone) | 15 | Ashalnd |
| Purified water | 300 | — |

2. Preparation of Glucose Pellet A (2-1) According to the formulation of Table 2, 2125.0 g of 120-mesh sieved glucose monohydrate, 250.0 g of MCC101 and 125.0 g of corn starch were uniformly mixed to obtain a powder;

(2-2) According to the formulation of Table 2, 50 g of PVPK29/32 was dissolved in 950 g of water to prepare a 5.0% PVPK29/32 binder solution;

(2-3) A coating granulator was started, and the obtained glucose core A was once added to the coating granulator. The rotating speed of turntable was set, and the powder obtained in the step (2-1) and the binder solution obtained in the step (2-2) were added continuously to the coating granulator in order to perform a laminating and powder-coating operation on the glucose core A, wherein the ratio of the total weight of the added powder to the total weight of the added glucose core A was 2.5:1, and the addition rate ratio of the powder to the binder solution was 1.70:1 (g·min$^{-1}$/g·min$^{-1}$). Then, the product was dried in a fluidized bed with an inlet air temperature of 50° C. and a drying time of 45 minutes to obtain the glucose pellet A, wherein the content of the glucose monohydrate in the laminated layer of the glucose pellet A was 81.73% (W/W).

TABLE 2

| | Raw material | Weight (g) |
|---|---|---|
| Powder to be added | Glucose monohydrate | 2125 |
| | MCC101 | 250 |
| | Starch | 125 |
| Binder solution | PVPK29/32 | 50 |
| | Water | 950 |

3. Preparation of Glucose Sustained-Release Pellet A (3-1) A 80.0% (W/W) ethanol solution was prepared from ethanol and water. According to the formulation of Table 3, 32.0 g of hydroxypropylcellulose (HPC-EF) was dissolved in 3776.0 g of the 80.0% (W/W) ethanol solution under constant stirring, then added 160.0 g of 20 centipoise (cP) ethylcellulose, and stirred continuously until the dissolution was completed to obtain a clear transparent solution;

(3-2) Before coating, according to the formulation of Table 3, 32.0 g of triethyl citrate (TEC) was added to the solution obtained by the step (3-1), stirred continuously and dissolved for 40 minutes, a coating solution was obtained;

(3-3) 1000.0 g of the glucose pellet A was placed in a bottom spray coating pan of a fluidized bed, and the fluidization state of the pellet was adjusted. After preheating at an inlet air temperature of 40° C. for a while, 4000.0 g of the coating solution obtained in the step (3-2) was continuously sprayed into the fluidized bed, and the glucose pellet A was subjected to a coating treatment. After the completion of the coating, the inlet air temperature was set to 45° C. and a drying was carried out for 30 minutes to obtain the glucose sustained-release pellet A.

TABLE 3

| Raw material | Action | Weight (g) |
|---|---|---|
| Ethylcellulose (20 cP) | Film-forming material | 160 |
| HPC-EF | Porogen | 32 |
| TEC | Platicizer | 32 |
| 80% (W/W) ethanol solution | Solvent | 3776 |

Example 2: Glucose Core B, Glucose Pellet B and Glucose Sustained-Release Pellet B 1. Preparation of Glucose Core B (1-1) Glucose monohydrate was pulverized, passed through a 120 mesh sieve, and the sieved portion was taken for subsequent steps. According to the formulation of Table 4, 750.0 g of glucose monohydrate and 230.0 g of MCC101 were added to a wet-mixing granulator and uniformly mixed to obtain an initial mixture;

(1-2) According to the formulation of Table 4, 20.0 g of PVPK29/32 was dissolved in 230.0 g of water to prepare a binder solution; the binder solution was sprayed into the wet-mixing granulator in atomization manner, and the glucose core B was obtained via granule preparation and granulation, and the content of the glucose monohydrate in the glucose core B was 60.22% (W/W).

TABLE 4

| Raw material | Weight (g) |
| --- | --- |
| Glucose monohydrate | 750 |
| MCC101 | 230 |
| PVPK29/32 | 20 |
| Water | 230 |

2. Preparation of Glucose Pellet B (2-1) According to the formulation of Table 5, 3062.5 g of 120-mesh sieved glucose monohydrate, 280.0 g of MCC101 and 157.5 g of corn starch were uniformly mixed to obtain a powder;

(2-2) According to the formulation of Table 5, 25 g of PVPK29/32 was dissolved in 975 g of water to prepare a 2.5% PVPK29/32 binder solution;

(2-3) A coating granulator was started, and the obtained glucose core B was added to the coating granulator at one time. The rotating speed of turntable was set, the powder obtained in the step (2-1) and the binder solution obtained in the step (2-2) were continuously added to the coating granulator in order to perform a laminating and powder-coating operation on the glucose core B, wherein the ratio of the total weight of the added powder to the total weight of the added glucose core B was 3.5:1, and the addition rate ratio of the powder to the binder solution was 1.78:1 ($g \cdot min^{-1}/g \cdot min^{-1}$). Then, the product was dried in a fluidized bed with an inlet air temperature of 50° C., and a drying time of 45 minutes to obtain the glucose pellet B, wherein the content of the glucose monohydrate in the laminated layer of the glucose pellet B was 86.0% (W/W).

TABLE 5

| | Raw material | Weight (g) |
| --- | --- | --- |
| Powder to be added | Glucose monohydrate | 3062.5 |
| | MCC101 | 280 |
| | Starch | 157.5 |
| Binder solution | PVPK29/32 | 25 |
| | Purified water | 975 |

3. Preparation of Glucose Sustained-Release Pellets B (3-1) A 80.0% (W/W) ethanol solution was prepared from Ethanol and water. According to the formulation of Table 6, 62.5 g of hydroxypropylmethylcellulose (HPMC-E5) was dissolved in 4625.0 g of the 80.0% (w/w) ethanol solution under constant stirring, then added 250.0 g of 10 centipoise (cP) ethylcellulose, and stirred continuously until the dissolution was completed to obtain a clear and transparent solution;

(3-2) Before coating, according to the formulation of Table 6, 62.5 g of dibutyl sebacate (DBS) was added to the solution obtained in the step (3-1), stirred continuously and dissolved for 40 minutes, a coating solution was obtained.

(3-3) 1000.0 g of the glucose pellet B was placed in a bottom spray coating pan of a fluidized bed, and the fluidization state of the pellet was adjusted. After preheating at an inlet air temperature of 42° C. for a while, 4000.0 g of the coating solution obtained in the step (3-2) was continuously sprayed into the fluidized bed to coat the glucose pellet B. After the completion of the coating, the inlet air temperature was set to 45° C. and a drying was carried out for 30 minutes to obtain the glucose sustained-release pellet B.

TABLE 6

| Raw material | Weight (g) |
| --- | --- |
| Ethylcellulose (10 cp) | 250 |
| HPMC-E5 | 62.5 |
| DBS | 62.5 |
| 80.0% (W/W) ethanol solution | 4625 |

Example 3: Glucose Core C, Glucose Pellet C and Glucose Sustained-Release Pellet C 1. Preparation of Glucose Core C (1-1) Glucose monohydrate was pulverized, passed through a 120 mesh sieve, and the sieved portion was taken for subsequent steps. According to the formulation of Table 7, 800.0 g of glucose monohydrate, 150.0 g of MCC101 and 20.0 g of corn starch were added to a wet-mixing granulator and uniformly mixed to obtain an initial mixture;

(1-2) According to the formulation of Table 7, 30.0 g of PVPK29/32 was dissolved in 270.0 g of water to prepare a binder solution; the binder solution was sprayed into the wet-mixing granulator in atomization manner, and the glucose core C was obtained via granule preparation and granulation, and in the glucose core C, the glucose monohydrate was present in an amount of 60.6% (W/W) and the starch was present in an amount of about 1.5% (W/W).

TABLE 7

| Raw material | Weight (g) |
| --- | --- |
| Glucose monohydrate | 800 |
| MCC101 | 150 |
| Corn starch | 20 |
| PVPK29/32 | 30 |
| Water | 270 |

2. Preparation of Glucose Pellet C (2-1) According to the formulation of Table 8, 3910.0 g of 120-mesh sieved glucose monohydrate, 715.0 g of MCC101 and 375.0 g of corn starch were uniformly mixed to obtain a powder;

(2-2) According to the formulation of Table 8, 72.0 g of PVPK29/32 was dissolved in 928.0 g of water to prepare a 7.2% PVPK29/32 binder solution;

(2-3) A coating granulator was started, and the obtained glucose core C was added to the coating granulator at one time. The rotating speed of turntable was set, and the powder obtained in the step (2-1) and the binder solution obtained in the step (2-2) were added continuously to the coating granulator, in order to perform a laminating and powder-coating operation on the glucose core C, wherein the ratio of the total weight of the added powder to the total weight of the added glucose core C was 5.0:1, and the addition rate ratio of the powder to the binder solution was 1.64:1 (g·min$^{-1}$/g·min$^{-1}$). Then, the product was dried in a fluidized bed with an inlet air temperature of 50° C. and a drying time of 45 minutes to obtain the glucose pellet C, in which the content of the glucose monohydrate in the laminated layer of the glucose pellet C was 77.5% (W/W).

TABLE 8

|  | Raw material | Weight (g) |
| --- | --- | --- |
| Powder to be added | Glucose monohydrate | 3910 |
|  | MCC101 | 715 |
|  | Starch | 375 |
| Binder solution | PVPK29/32 | 72 |
|  | Water | 928 |

3. Preparation of Glucose Sustained-Release Pellet C (3-1) A 80.0% (W/W) ethanol solution was prepared from ethanol and water. According to the formulation of Table 9, 18.75 g of PVPK29/32 was dissolved in 3536.25 g of the 80.0% (W/W) ethanol solution under constant stirring, then added 150.0 g of 45 centipoise (cP) ethylcellulose, and stirred continuously until the dissolution was completed to obtain a clear and transparent solution;

(3-2) Before coating, according to the formulation of Table 9, 45.0 g of tributyl citrate (TBC) was added to the solution obtained by the step (3-1), stirred continuously and dissolved for 40 minutes, a coating solution was obtained;

(3-3) 1000.0 g of the glucose pellet C was placed in a bottom spray coating pan of a fluidized bed, and the fluidization state of the pellet was adjusted. After preheating for a while, 3750.0 g of the coating solution obtained in the step (3-2) was continuously sprayed into the fluidized bed, and the glucose pellets were subjected to a coating treatment. After the completion of the coating, the inlet air temperature was set to 45° C. and a drying was carried out for 30 minutes to obtain the glucose sustained-release pellet C.

TABLE 9

| Component | Weight (g) |
| --- | --- |
| Ethylcellulose (45 cP) | 150 |
| TBC | 45 |
| PVPK29/32 | 18.75 |
| 80% (W/W) ethanol solution | 3536.25 |

Comparative Example 1: Glucose Core I (Effect of Glucose Monohydrate Content in Core)

The glucose monohydrate was pulverized, passed through a 120 mesh sieve, and the sieved portion was taken for subsequent steps. According to the formulation of Table 10, 950.0 g of glucose monohydrate and 50.0 g of MCC101 were added to a wet-mixing granulator and mixed uniformly; according to the formulation of Table 10, 12.36 g of PVPK29/32 was dissolved in 93.58 g of purified water to prepare a binder solution. The rest steps were carried out in the same manner as in Example 1, to obtain a glucose core I, wherein the content of the glucose monohydrate in the glucose core I was 85.29% (W/W).

The results of particle size distribution detection of the glucose core I are shown in Test Example 1.

TABLE 10

| Raw material | Weight (g) |
| --- | --- |
| Glucose monohydrate | 950.0 |
| MCC101 | 50.0 |
| PVPK29/32 | 12.36 |
| Purified water | 93.58 |

Comparative Example 2: Glucose Core II (Effect of Particle Size of Glucose Monohydrate in Core)

The experiment was carried out by using 100-mesh sieved (<150 μm) glucose monohydrate, and the rest steps were carried out in the same manner as in Example 1 to obtain the glucose core II.

The results of surface state detection of the glucose core II are shown in Test Example 2.

Comparative Example 3: Glucose Pellet III (Effect of Glucose Monohydrate Content in Laminated Layer)

According to the formulation of Table 11, 1500.0 g of 120-mesh sieved glucose monohydrate, 625.0 g of MCC101 and 375.0 g of corn starch were uniformly mixed to obtain a powder; according to the formulation of Table 11, 50.0 g of PVPK29/32 was dissolved in 950.0 g of water to obtain a 5.0% PVPK29/32 binder solution; the rest steps were carried out in the same manner as in Example 1 to obtain the glucose pellet III, in which the glucose content in the laminated layer of the glucose pellet III was 58.82% (W/W).

The results of release effect of a glucose sustained-release pellet III prepared from the glucose pellet III are shown in Test Example 3.

TABLE 11

|  | Raw material | Weight (g) |
| --- | --- | --- |
| Powder to be added | Glucose monohydrate | 1500 |
|  | MCC101 | 625 |
|  | Corn starch | 375 |
| Binder solution | PVPK29/32 | 50 |
|  | Water | 950 |

Comparative Example 4: Glucose Pellet IV (Effect of Particle Size of Glucose Monohydrate in Laminated Layer)

According to the formulation of the laminated layer, a glucose monohydrate passed through a 100 mesh sieve (<150 μm) was taken for the experiment, and the rest steps were carried out in the same manner as in Example 1 to obtain the glucose pellet IV.

The results of surface state detection of the glucose pellet IV are shown in Test Example 2.

Comparative Example 5: Glucose Pellet V and Glucose Pellet VI (Effect of Particle Size of Glucose Core)

(1) Preparation and Particle Size Distribution Detection of the Glucose Pellet V According to the formulation of Table 12, 614.0 g of glucose monohydrate and 371.0 g of MCC101 were uniformly mixed in a wet-mixing granulator, and 5.0 g of PVPK-30 was dissolved in 100.0 g of purified water to prepare a binder solution, and the rest steps were carried out in accordance with Example 1 to obtain the core, in which the obtained core had a particle size smaller than that of the glucose core A.

TABLE 12

| Raw material | Weight (g) |
| --- | --- |
| Glucose monohydrate | 614.0 |
| MCC101 | 371.0 |
| PVPK29/32 | 5.0 |
| Purified water | 100.0 |

The glucose pellet V was prepared in accordance with the method of Example 1 from the prepared glucose core having a smaller particle size. After sampling, the detection was carried out using an Olympus SZXZ-ILLB optical microscope in combination with an accessory detection software, and it was observed that the glucose cores in the glucose pellet V had mutual adhesion phenomenon.

(2) Preparation and Particle Size Distribution Detection of Glucose Pellet VI

Glucose pellet VI was prepared from the glucose core I obtained in Comparative Example 1, and prepared in accordance with Example 1. The results of particle size distribution detection of the glucose pellet VI are described in Test Example 1.

Comparative Example 6: Glucose Core VII (Effect of Starch Content in Core)

According to the formulation of Table 13, 614.0 g of 120-mesh sieved glucose monohydrate, 195.0 g of starch and 176.0 g of MCC101 were added to a wet-mixing granulator and mixed uniformly, and the rest steps were carried out with reference to Example 1, to obtain the glucose core VII, wherein the starch content was about 14.76% (W/W).

The results of particle size distribution detection of glucose core VII are shown in Test Example 1.

TABLE 13

| Raw material | Weight (g) |
| --- | --- |
| Glucose monohydrate | 614 |
| MCC101 | 176 |
| Starch | 195 |
| PVPK29/32 | 15 |
| Water | 300 |

Comparative Example 7: Glucose Pellet VIII and Glucose Pellet IX (Effect of Powder/Core Weight Ratio)

(1) Preparation and Particle Size Detection of Glucose Pellet VIII:

In the laminating and powder-coating operation of the glucose core, the ratio of the total weight of the added powder to the total weight of the added glucose core A was 1:1; the rest steps were carried out with reference to Example 1; and the glucose pellet VIII was obtained.

(2) Preparation and Particle Size Detection of Glucose Pellet IX:

In the laminating and powder-coating operation of the glucose core, the ratio of the total weight of the added powder to the total weight of the added glucose core A was 8:1; the rest steps were carried out with reference to Example 1; and the glucose pellet IX was obtained.

The results of particle size distribution detection of the glucose pellet VIII and the glucose pellet IX are shown in Test Example 1.

Comparative Example 8: Glucose Pellet X and Glucose Pellet XI (Effect of Ratio of Powder Supplying Rate and Slurry Spraying Rate)

(1) Preparation and Particle Size Detection of Glucose Pellet X:

In the laminating and powder-coating operation of the glucose core, the addition rate ratio of the powder and the binder solution was 1:1 (g·min$^{-1}$/g·min$^{-1}$), and the rest steps were carried out with reference to Example 1, to obtain the glucose pellet X. After sampling, the detection was carried out using an Olympus SZXZ-ILLB optical microscope combined with an accessory detection software, and it was observed that the glucose cores in the pellet adhered to each other.

(2) Preparation, Particle Size Detection and Surface State Detection of Glucose Pellet XI:

in the laminating and powder-coating operation of the glucose core, the addition rate ratio of the powder to the binder solution was 3:1 (g·min$^{-1}$/g·min$^{-1}$), the rest steps were carried out with reference to Example 1 to obtain the glucose pellet XI.

The results of particle size distribution detection of the glucose pellet XI are shown in Test Example 1, and the results of surface state detection of that are shown in Test Example 2.

Test Example 1: Particle Size Distribution Test (1) Particle Size Distribution of Glucose Core The particle size distributions of the glucose cores of Example 1, Comparative Example 1, and Comparative Example 6 were detected, and the detection method was to measure the particle sizes of the cores by Olympus SZXZ-ILLB type optical microscope combined with an accessory detection software. The particle size distribution of the core was determined from the measured particle sizes of the largest core and the smallest core, and the results are shown in Table 14.

TABLE 14

| Test | Example 1 | Comparative Example 1 | Comparative Example 6 |
| --- | --- | --- | --- |
| Core | Core A | Core I | Core VII |
| Particle size of the largest core | 0.25 mm | 0.38 mm | 0.42 mm |
| Particle size of the smallest core | 0.15 mm | 0.18 mm | 0.13 mm |
| Particle size distribution | 0.15 mm~ 0.25 mm | 0.18 mm~ 0.38 mm | 0.13 mm~ 0.42 mm |

The results showed:

The core I of Comparative Example 1 had a larger particle diameter than the core A of Example 1, and its particle size distribution was not narrower than that of the core A. It could be seen that the excessive content of glucose monohydrate in core resulted in a larger particle size of the core and a broader particle size distribution.

The largest particle size of the core VII of Comparative Example 6 was larger than that of the core A of Example 1, and its particle size distribution was broader, much broader than the particle size distribution of the core A. It could be seen that the excessive starch content in core resulted in a larger particle size and a broader particle size distribution of the core.

(2) Particle Size Distribution of Glucose Pellet

The particle size distributions of the glucose pellets in Example 1, Comparative Example 5 (2), Comparative Example 7, and Comparative Example 8 (2) were detected, and the detection method was to perform screening by Chinese National Standard sieves (GB/T6005-2008, Test Sieves, basic sizes of metal wire mesh, perforated plate and electroformed sheet mesh), to weigh the masses of pellets in different particle size ranges, and to calculate the mass proportions thereof, and the results are shown in Table 15.

TABLE 15

| Test | Example 1 | Comparative Example 5 (2) | Comparative Example 7 | | Comparative Example 8 (2) |
|---|---|---|---|---|---|
| Kind of pellet | Pellet A | Pellet VI | Pellet VIII | Pellet IX | Pellet XI |
| >20 mesh | 2.6% | 15.5% | 0.3% | 45.8% | 0.9% |
| 20~30 mesh | 68.2% | 70.1% | 8.6% | 38.4% | 41.4% |
| 30~40 mesh | 24.4% | 12.6% | 35.2% | 12.8% | 25.4% |
| 40~50 mesh | 3.1% | 1.2% | 40.7% | 2.7% | 18.7% |
| <50 mesh | 1.7% | 0.6% | 15.2% | 0.3% | 13.6% |

The results showed:

The particle size of the glucose pellet of Comparative Example 5 (2) was larger than that of Example 1, mainly because that the proportion of the large particle size pellets increased, i.e. the proportion of the 30 to 40 mesh pellets decreased, and the proportion of the pellets larger than 20 mesh increased significantly. It could be seen that the glucose pellet prepared by the core with larger particle size had a larger particle size.

The particle size of the glucose pellet of Comparative Example 7 (1) was smaller than that of Example 1. When the ratio of the total weight of the powder to the total weight of the core was 1:1, the pellets were mainly of 30 to 50 mesh. It could be seen that when other conditions were same and the weight ratio of powder/core was relatively smaller, the pellet would have a smaller particle size.

The glucose pellets of Comparative Example 7 (2) had a larger particle size than that of Example 1, in which about 45.8% of the pellets had a size larger than 20 mesh, and 38.4% of the pellets had a size between 20 to 30 mesh. It could be seen that when the other conditions were same and the weight ratio of powder/core was relatively larger, the pellet would have a larger particle size.

The particle size of the glucose pellet of Comparative Example 8 (2) was smaller than that of Example 1, in which the proportion of the pellets smaller than 40 mesh was 32.3%, which was significantly more than 4.8% of Example 1. It could be seen that when other conditions were same and the ratio of powder feeding rate to slurry spraying rate was relatively larger, the pellet would have a smaller particle size.

Test Example 2: Surface State Test (1) Surface State of Glucose Cores

The surface states of the glucose cores of Example 1 and Comparative Example 2 were detected. The detection method was to sample, and to observe under an optical microscope, and the results are shown in Table 16.

TABLE 16

| Test | Example 1 | Comparative Example 2 |
|---|---|---|
| Kind of core | Glucose core A | Glucose core II |
| Test results | Core had flat surface without protrusions and burrs. | Some cores had extremely uneven surfaces adhered with glucose crystals, and there were some ungranulated glucose crystals in the cores. |

The results showed that when the glucose monohydrate used in the core preparation process had a larger particle size and a broader particle size distribution, it would had a great influence on the surface state of the core.

(2) Surface State of Glucose Pellets

The surface states of the glucose pellets A, IV, and XI of Example 1, Comparative Example 4, and Comparative Example 8 (2) were detected, in which the detection method was to sample and to observe under an optical microscope, and the results are shown in Table 17.

TABLE 17

| Test | Example 1 | Comparative Example 4 | Comparative Example 8 (2) |
|---|---|---|---|
| Pellet | Pellet A | Pellet IV | Pellet XI |
| Test results | Pellet had a smooth and flat surface without burrs. | Some pellets had rugged surfaces caused by glucose crystals. | Pellet had rough surface with poor flatness, and the surface of pellet was more easy to wear. |

The results showed:

The larger particle size and the broader particle size distribution of the glucose monohydrate in the laminated layer would greatly affect the surface state of the pellet, which mainly manifested in that the pellet surface had a deteriorated flatness, the pellet surface became more uneven, and some pellets even had surfaces adhered with glucose crystals.

If the ratio of the powder supplying rate to the slurry spraying rate was too large, it would affect the efficient and complete spreading of the powder on the core surface. Then it would affect the surface flatness and result in an increased roughness on the pellet surface.

Test Example 3: Test of Sustained-Release Effect

The release effects of the sustained-release pellets of Examples 1 to 3, and the sustained-release pellet III prepared from the pellet III of Comparative Example 3 (referring to the preparation method of the sustained-release pellet in Example 1) were detected, in which the content and the dissolution rate of drug in the sustained-release pellet were used as evaluation indexes.

(1) Determination of the Drug Content of the Sustained-Release Pellet by High Performance Liquid Phase Chromatography (Determination by High Performance Liquid Phase Chromatography According to Chinese Pharmacopoeia, 2015 Ed, General Rules 0512):

Chromatographic conditions: Waters Xbridge™ Amide (50×4.6 mm, 5 μm) hydrophilic column; acetonitrile-water-triethylamine (70:30:0.2) as mobile phase, isocratic elution; flow rate 1.0 mL/min; column temperature: 45° C.; injection volume 20 μL; detection with Waters2424ELSD; drift tube temperature 70° C., sprayer heating 70%, pressure 35 psi, gain 10.

Determination method: An appropriate amount of glucose sustained-release pellets ($W_{sample}$, g), which was equivalent to about 100 mg of glucose, was sampled, and placed in a 100 mL ($V_1$, mL) volumetric flask, acetonitrile in an appropriate amount was added, ultrasonicated and shaken for about 5 minutes to swell the coating; then 30 mL of water was added, ultrasonicated and shaken for about 5 minutes until the main drug was completely dissolved, diluted to the mark with acetonitrile, shaken uniformly, filtered, and 5 mL ($V_2$, mL) of the filtrate was taken and placed in a 50 mL ($V_3$, mL) volumetric flask, diluted to the mark with 70% acetonitrile, shaken uniformly, and used as a sample solution to be determined according to the above chromatographic conditions and test parameters. Additionally, 90 mg ($W_{reference}$, mg) of anhydrous glucose was taken as a reference substance, weighed accurately, placed in a 100 mL volumetric flask, 30 mL of water was added, then ultrasonicated to dissolve the anhydrous glucose, and acetonitrile was added to the mark for dilution, so as to obtain a stock solution; 1 mL, 2 mL, 5 mL, 7 mL, 10 mL of the stock solution were accurately measured and taken, placed in five 50 mL volumetric flasks respectively, diluted with 70% acetonitrile-water to the mark, and used as standard curve solutions, and the determination thereof was carried out by the same method. The drug contents of the sustained release pellets were calculated, and the results are shown in Table 18.

(2) Determination of Drug Dissolution Rate of Sustained-Release Pellets (Chinese Pharmacopoeia, 2015 Edition, Part IV, General Rules 0931, Second Method):

An appropriate amount of glucose sustained-release pellets ($S_{standard}$, mg), equivalent to about 100 mg of glucose, was taken, 500 mL ($V_4$, mL) of water was as dissolution medium, rotation speed was set to 50 rpm, and the determination was carried out according to the method. After 1 hour, 2 hours, 4 hours, 6 hours, 8 hours, 10 hours, 12 hours, 5 mL of the solutions were taken respectively, filtered, and 3 mL ($V_5$, mL) of the filtrate was taken and added to 10 mL ($V_6$, mL) volumetric flask, diluted with acetonitrile to the mark, shaken uniformly, and used as a sample solution to be tested. And the dissolution medium with the same volume and the same temperature was added immediately. Anhydrous glucose 90 mg ($W_{reference}$, mg) as reference substance was taken, accurately weighed, placed in a 100 mL volumetric flask, dissolved in water under ultrasonication and diluted to mark, and used as a stock solution. 1 mL, 2 mL, 5 mL, 7 mL, 10 mL of the stock solution were taken and accurately measured, placed in five 50 mL volumetric flasks respectively, diluted to mark with water, shaken well, and 3 mL of each of reference substance solutions with the above concentrations was accurately transferred to a 10 mL volumetric flask, diluted to mark with acetonitrile, shaken well, and used as a reference solution. According to the chromatographic conditions in the above item (1), 100 μL of each of the sample solutions and each of the reference solutions were accurately measured and injected into a liquid chromatograph for determination respectively. The log $A_{reference}$ of each reference solution was used as the ordinate, and the log $c_{reference}$ of that was used as the abscissa to plot a standard curve, wherein $A_{reference}$ indicated the peak area measured for each reference solution, and the $c_{reference}$ indicated the concentration of the corresponding reference solution. The peak area $A_{sample}$ of the sample solution was substituted into the standard curve to obtain the concentration $c_{sample}$ of the sample solution.

Figure 1:
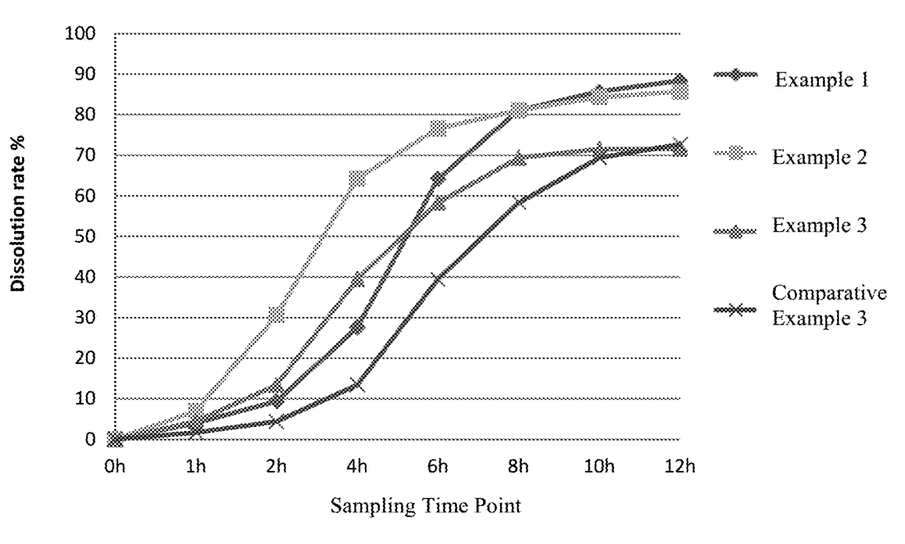
FIG. 1 is a graph showing the dissolution rate-time curves of different sustained-release pellets in Test Example 3.

The dissolution rate of the sample was calculated according to the following formula. The results are shown in Table 19 and FIG. 1.

$$\text{Dissolution rate (\%)} = \frac{c_{sample} \times V_4 \times V_6}{S_{standard} \times 1000 \times V_5} \times 100\%$$

wherein, 1000 represents a conversion rate between mg and g.

TABLE 18

| Test | Example 1 | Example 2 | Example 3 | Comparative Example 3 |
|---|---|---|---|---|
| Sustained-release pellet | Sustained-release pellet A | Sustained-release pellet B | Sustained-release pellet C | Sustained-release pellet III |
| Drug content (W/W) | 63.94% | 61.61% | 64.95% | 49.35% |

TABLE 19

| | | Sampling time point | | | | | | | |
|---|---|---|---|---|---|---|---|---|---|
| | | 0 h | 1 h | 2 h | 4 h | 6 h | 8 h | 10 h | 12 h |
| Dissolution rate (%) | Sustained-release pellet A | 0.0 | 4.0 | 9.4 | 27.6 | 64.2 | 81.1 | 85.7 | 88.4 |
| | Sustained-release pellet B | 0.0 | 4.4 | 13.4 | 39.5 | 58.3 | 69.4 | 71.5 | 71.6 |
| | Sustained-release pellet C | 0.0 | 7.0 | 30.6 | 64.3 | 76.6 | 81.1 | 84.3 | 85.7 |
| | Sustained-release pellet III | 0.0 | 1.7 | 4.4 | 13.4 | 39.5 | 58.3 | 69.4 | 72.7 |

The results showed:

According to the results of the drug content and dissolution rate tests of the sustained-release pellets, the drug content of the sustained-release pellet III with less glucose content in the laminated layer was much lower than those of the sustained-release pellets of Examples 1 to 3.

Compared with the sustained-release pellets of Examples 1 to 3, the sustained-release effect of the sustained-release pellet III of Comparative Example 3 was significantly worse, mainly due to the slower release in the early stage and the incomplete release in the later stage.

The sustained-release pellet III of Comparative Example 3 had a low drug content, and more sustained-release pellets were required to be loaded under the same specification, that was, the loading amount increased. Moreover, the utilization rate of glucose as main drug was not high due to that some main drug was not completely released in the later stage of release.

It is apparent that the above-described examples are merely illustration of the invention, and are not intended to limit the embodiments of the invention. Other variations or modifications of the various forms of the invention may be made by those skilled in the art in light of the above description. There is no need and no way to exhaust all of the embodiments. Obvious changes or variations resulting therefrom are still within the scope of the invention.

What is claimed is:

1. A glucose core comprising the following components:
   a glucose, and/or a glucose hydrate,
   a first additional agent as a diluent, and
   a second additional agent as a binder;
   wherein, the glucose and/or the glucose hydrate is present in the glucose core in an amount of <85% as calculated by weight percentage;
   the glucose and/or the glucose hydrate is a particle consisting of a size sieved through a mesh of 110, 120, 130, 140 or 150, as measured by Chinese National Standard sieves; and the glucose core has a particle diameter of 100 to 300 μm.

2. The glucose core according to claim 1, wherein the diluent comprises a microcrystalline cellulose, and optionally a starch;
   wherein the starch is present in the glucose core in an amount of 0% to 13% as calculated by weight percentage.

3. A glucose pellet comprising the glucose core according to claim 1, and a laminated layer coating the glucose core; wherein the laminated layer comprises the following components:
   a glucose, and/or a glucose hydrate,
   a first additional agent as a diluent, and
   a second additional agent as a binder.

4. The glucose pellet according to claim 3, wherein the glucose, and/or the glucose hydrate is present in the laminated layer in an amount greater than the amount of the glucose, and/or the glucose hydrate in the glucose core.

5. A glucose sustained-release pellet comprising the glucose pellet according to claim 3, and a sustained-release coating on the glucose pellet;
   wherein the sustained-release coating comprises a first agent as a porogen, a second agent as a film-forming agent, and a third agent as a plasticizer.

6. The glucose sustained-release pellet according to claim 5, wherein, as calculated by weight percentage,
   the film-forming agent is present in the sustained-release coating in an amount of 60% to 80%;
   the porogen is present in the sustained-release coating in an amount of 8% to 20%; and,
   the plasticizer is present in the sustained-release coating in an amount of 10% to 23%.

7. A method for preparing the glucose core according to claim 1, comprising the following steps:
   (1-1) mixing a glucose, and/or a glucose hydrate particle consisting of a size sieved through a mesh of 110, 120, 130, 140 or 150, with a first additional agent as a diluent to obtain a mixture 1;
   (1-2) dissolving a second additional agent as a binder in a solvent to form a binder solution;
   (1-3) mixing the binder solution with the mixture 1 to obtain a mixture 2; and
   (1-4) granulating the mixture 2 to obtain the glucose core.

8. A method for preparing the glucose pellet according to claim 3, comprising the steps of preparing a laminated layer as follows:
   (2-1) mixing a glucose, and/or a glucose hydrate with a first additional agent as a diluent to obtain a mixture;
   (2-2) dissolving a second additional agent as a binder in a solvent to form a binder solution; and
   (2-3) performing lamination treatment of the glucose core with the mixture and the binder solution, and drying to obtain the glucose pellet.

9. The method for preparing the glucose pellet according to claim 8, wherein the method further comprises the following steps of coating the glucose pellet:
   (3-1) formulating ethanol and water into an ethanol-water solution, dissolving a first agent as a porogen in the ethanol-water solution, and adding a second agent as a film-forming agent to obtain a solution;
   (3-2) dissolving a third agent as a plasticizer in the solution obtained in the step (3-1) to obtain a coating solution;
   (3-3) coating the glucose pellet with the coating solution obtained in the step (3-2), and drying to obtain a glucose sustained-release pellet.

10. A pharmaceutical composition comprising the glucose pellet according to claim 3.

11. A method for treating a glycogen storage disease or a diabetes, comprising a step of administering to a subject in need thereof an effective amount of the glucose pellet according to claim 3.

12. A method for inhibiting glycogen accumulation or maintaining blood glucose stability, comprising a step of administering to a subject in need thereof an effective amount of the glucose pellet according to claim 3.

13. The glucose pellet according to claim 3, wherein the glucose, and/or the glucose hydrate is present in the laminated layer in an amount of ≥70%, as calculated by weight percentage.

14. The glucose pellet according to claim 3, wherein the glucose, and/or the glucose hydrate is a particle consisting of a size sieved through a mesh of 110, 120, 130, 140 or 150 in the laminated layer, as measured by Chinese National Standard sieves.

15. The method for preparing the glucose pellet according to claim 8, wherein, in the step (2-3), the weight ratio of the mixture to the glucose core is (1.5-6):1.

16. The method for preparing the glucose pellet according to claim 8, wherein, in the step (2-3), an addition rate ratio of the mixture to the binder solution is (1.36-2.25):1 (g·min$^{-1}$/g·min$^{-1}$).

17. A method for treating a glycogen storage disease or a diabetes, comprising a step of administering to a subject in need thereof an effective amount of the pharmaceutical composition according to claim 10.

18. A method for inhibiting glycogen accumulation or maintaining blood glucose stability, comprising a step of administering to a subject in need thereof an effective amount of the pharmaceutical composition according to claim 10.

* * * * *